(12) United States Patent
Rouquet et al.

(10) Patent No.: US 6,258,345 B1
(45) Date of Patent: Jul. 10, 2001

(54) STABLE TOPICAL COMPOSITION COMPRISING A SOLID ELASTOMERIC ORGANOPOLYSILOXANE AND SPHERICAL PARTICLES

(75) Inventors: Violaine Rouquet, Eze; Jean-Claude Contamin, Cantaron, both of (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 09/163,407

(22) Filed: Sep. 30, 1998

(30) Foreign Application Priority Data

Oct. 1, 1997 (FR) .................................................. 97 12223

(51) Int. Cl.⁷ ............................ A61K 7/025; A61K 7/42; A61K 7/021; A61K 7/00
(52) U.S. Cl. ................................. 424/64; 424/59; 424/63; 424/401; 514/845; 514/846
(58) Field of Search ................................. 424/401, 64, 59, 424/63; 514/846, 845

(56) References Cited

U.S. PATENT DOCUMENTS 4,983,377   1/1991   Murphy et al. .

5,266,321   11/1993   Shukuzaki et al. .

FOREIGN PATENT DOCUMENTS

| 0 295 886 | 12/1988 | (EP) . |
| 0 834 305 | 4/1998 | (EP) . |
| 94/17774 | 8/1994 | (WO) . |
| 97/32560 | 9/1997 | (WO) . |

OTHER PUBLICATIONS

R. Keraudy, "Les Poudres Polyamides Dans Les Formulations Cosmétiques", Parfums, Cosmétiques, Arômes, No. 52, Sep. 1983, pp. 83–85.

*Primary Examiner*—Diana Dudash
*Assistant Examiner*—Alysia Berman
(74) *Attorney, Agent, or Firm*—Oblon, Spivak, McClelland, Maier & Neustadt, P.C.

(57) ABSTRACT

A stable topical composition, which can be used in the cosmetic or dermatological fields, comprising at least one liquid fatty phase in combination with a solid phase representing at least 10% of the total weight of the fatty phase and further comprising a partially or completely crosslinked elastomeric organopolysiloxane and spherical polymeric particles with a particle diameter of less than 10 $\mu$m.

45 Claims, No Drawings

STABLE TOPICAL COMPOSITION COMPRISING A SOLID ELASTOMERIC ORGANOPOLYSILOXANE AND SPHERICAL PARTICLES

The invention relates to a stable topical composition comprising a liquid fatty phase in combination with a partially or completely crosslinked elastomeric organopolysiloxane. This composition is more especially intended for the cosmetic or dermatological field. It can constitute in particular a composition for caring for, treating, making up or removing make-up from the skin of the face or of the body, keratinous fibres (hair, eyelashes, eyebrows) and mucous membranes, such as the lips and the inner surfaces of the eyelids, of human beings.

It is known to use, in cosmetic or dermatological compositions, spherical particles, such as silica particles, for the purpose of conferring a degree of consistency on these compositions. Reference may in particular be made to the document by Shiseido EP-A-765,656. In these compositions, the higher the amount of particles, the thicker the composition. In addition, these particles have the property of absorbing fatty substances, and conferring a non-greasy appearance on these compositions, even in the presence of a large amount of fatty substances. This type of composition is much appreciated by consumers, in particular those with a skin with a greasy tendency. Unfortunately, the higher the amount of silica particles, the greater the instability of the composition. In addition, these particles confer a very rough and dry feel on the composition, thus limiting the use of this type of composition.

The inventors have developed a stable composition with a high level of spherical particles which does not exhibit the above disadvantages, while retaining the non-greasy property.

More specifically, the invention relates to a composition comprising at least one liquid fatty phase associated with a solid phase comprising particles of at least one partially or completely crosslinked elastomeric organopolysiloxane, wherein the particles in the solid phase represent at least 10% of the total weight of the fatty phase and, in addition, the composition comprises spherical organic particles with a particle diameter of less than 10 $\mu$m.

Another subject-matter of the invention is the use, in a composition comprising at least one liquid fatty phase associated with solid phase containing particles and further comprising spherical organic particle with a particle diameter of less than 10 $\mu$m, the particles in the solid phase representing at least 10% of the total weight of the fatty phase, of particles of one or more partially or completely crosslinked elastomeric organopolysiloxanes, in order to stabilize and/or to render homogeneous the said composition.

A further subject-matter of the invention is a process for the stabilization and/or homogenization of a composition comprising at least one liquid fatty phase associated with a solid phase containing particles, the particles in the solid phase representing at least 10% of the total weight of the fatty phase and further comprising spherical particles with a particle diameter of less than 10 $\mu$m, which process comprises using particles of at least one partially or completely crosslinked elastomeric organopolysiloxane in the solid phase.

By virtue of the presence of one or more solid elastomeric organopolysiloxanes, it is possible to obtain stable compositions comprising a high amount of spherical organic particles which can represent up to 40% by weight (as active material) of the total fatty phase.

"Stable composition" should be understood as meaning maintenance of the homogeneous appearance of the composition, without demixing, precipitation or flocculation of the particles, for at least 2 months at 45° C. "Elastomeric" is understood to mean a flexible and deformable material having viscoelastic properties and exhibiting in particular the consistency of a sponge or of a flexible sphere.

"Liquid fatty phase" should be understood as meaning a fatty phase which is liquid at room temperature, often known as oily phase.

According to the invention, it is additionally possible to combine, with the liquid fatty phase, a fatty phase which is solid or semi-solid at room temperature, for the purpose of modifying the rheology of the composition.

Although the invention applies to any technical field, it is intended more especially for the cosmetic and dermatological fields. The composition of the invention is well suited to topical application.

The elastomeric organopolysiloxanes of the composition according to the invention exhibit a notable oil-gelling power. They are not desiccating to the skin and contribute good cosmetic properties. These novel elastomers result in compositions which are comfortable on application, soft and nonsticky to the touch. This softness is due in particular to the texture of the organopolysiloxanes.

The combination of the invention also makes it possible to obtain care or make-up products intended in particular for softening blemishes of the contours of the skin, while contributing a natural appearance to it.

Preferably, the spherical organic particles have a particle diameter of less than 5 $\mu$m. Particle diameter should be understood as meaning the diameter of the unit particles. This is because the spherical particles may have a tendency to agglomerate, resulting in aggregates which can have particle diameters of greater than 5 $\mu$m, or even greater than 10 $\mu$m.

In particular, representative spherical organic particles to which the invention applies are polymeric particles chosen from microbeads of methylsilsesquioxane resins, such as, for example, those sold by Toshiba Silicone under the name Tospearl 145A®, microbeads of poly(methyl methacrylate) s, such as in particular those sold by Seppic under the name Micropearl M 100®, spherical particles of crosslinked polydimethylsiloxanes, such as in particular those sold by Dow Corning Toray Silicone under the name Trefil E 506 C® or Trefil E-505C®, spherical particles of polyamide and more especially of Nylon 12, such as in particular those sold by Atochem under the name Orgasol 2002 D Nat C05®, polystyrene microspheres, such as, for example, those sold by Dyno Particles under the name Dynospheres®, and their mixtures.

The "Trefils" are in particular spherical particles of crosslinked polymers disclosed in Application EP-A-0,295,886 of Toray Silicone Company. According to this application, they are obtained by addition and crosslinking reaction, in the presence of a catalyst of the platinum type, of at least:

(a) one organopolysiloxane having at least two lower alkenyl groups per molecule; and
(b) one organopolysiloxane having at least two hydrogen atoms bonded to a silicon atom per molecule.

The elastomeric organopolysiloxanes of the composition of the invention exhibit a three-dimensional structure. Depending on the level of the liquid fatty phase used in combination with these organopolysiloxanes, the latter are converted from a product with a spongy appearance, when they are used in the presence of low contents of fatty phase, to a more or less homogeneous gel, in the presence of larger amounts of fatty phase. The gelling of the liquid fatty phase by these elastomers can be complete or partial.

The elastomers of the composition of the invention are generally carried in the form of a gel composed of an elastomeric organopolysiloxane with a three-dimensional structure included in at least one hydrocarbon-comprising oil and/or one silicone oil.

The elastomeric organopolysiloxanes of the composition according to the invention can also be chosen from those disclosed in U.S. Pat. No. 5,266,321 of Kobayashi Kose, the disclosure of which is specifically incorporated by reference herein. According to this patent, they are chosen in particular from:

i) organopolysiloxanes comprising $R_2SiO$ and $RSiO_{1.5}$ units and optionally $R_3SiO_{0.5}$ and/or $SiO_2$ units in which the R radicals, independently of one another, represent a hydrogen, an alkyl, such as methyl, ethyl or propyl, an aryl, such as phenyl or tolyl, or an unsaturated aliphatic group, such as vinyl, the ratio by weight of the $R_2SiO$ units to the $RSiO_{1.5}$ units ranging from 1/1 to 30/1;

ii) organopolysiloxanes which are insoluble and which can be swollen in a silicone oil, obtained by addition of an organohydropolysiloxane (1) and of an organopolysiloxane (2) having unsaturated aliphatic groups, so that the amount of hydrogen or of unsaturated aliphatic groups in (1) and (2) respectively is between 1 and 20 mol % when the organopolysiloxane is non-cyclic and between 1 and 50 mol % when the organopolysiloxane is cyclic.

The organopolysiloxanes which are the subject-matter of the invention are, for example, those sold under the names KSG6® of Shin-Etsu or Gransil of Grant Industries (SR-CYC®, SR DMF10®, SR-DC556®) or those sold in the form of already constituted gels (KSGI5®, KSG17®, KSGI6®, KSG18® of Shin-Etsu, Gransil SR 5CYC® gel, Gransil SR DMF 10 gel®, Gransil SR DC 556 gel®, SF 1204® and JK 113® of General Electric. Use may also be made of a mixture of these commercial products.

The combined elastomeric organopolysiloxane particles and spherical particles represent at least 10% (as active material) of the total weight of the (liquid+solid) fatty phase and better still at least 20% (as active material). This combination can, in addition, represent up to 40% (as active material) of the total weight of the fatty phase.

The stability and the homogeneity of the composition depend on the amount of spherical particles and increase with the amount of elastomeric organopolysiloxane. By way of indication, the ratio by weight of the spherical particles to the elastomeric organopolysiloxane particles (as active material) is chosen within the range from 0.25:1 to 1 and better still from 0.4 to 0.7. The amount of spherical particles (as active material) preferably varies from 2% to 20% of the total weight of the composition and the amount of elastomeric organopolysiloxane particles (as active material) preferably varies from 2% to 20% of the total weight of the composition.

The composition advantageously comprises a continuous fatty phase. By virtue of the specific particles present in the composition, this type of composition is neither greasy to the touch and on application, nor oily. In addition, this composition has great softness. Thus, the composition of the invention can advantageously be an anhydrous gel or a water-in-oil (W/O) emulsion. However, it can be provided in the form of an oil-in-water emulsion. In addition, it is provided in the form of a cream.

Depending on the amount of particles used, it is possible to obtain compositions which are more or less viscous, stable and homogeneous over time. In particular, the composition can have a dynamic viscosity, measured at room temperature with a device of the Rheomat RM 180 (Mettler) type, ranging from 2 to 20 Pa·s.

The composition of the invention advantageously constitutes a care or make-up base to be applied to the skin or the lips before the care or make-up product. In particular, it makes it possible to extend the hold over time of the care or makeup composition, which is particularly advantageous for foundation products, products for concealing rings under the eyes, lip glosses and sun protection products. It can also be used as a composition for rendering the skin matt which is suited to greasy skin.

The oily fatty phase used in combination with the elastomeric organopolysiloxanes of the invention can comprise hydrocarbon-comprising oils and/or silicone oils.

Mention may in particular be made, as hydrocarbon-comprising oils which can be used in the invention, of:

hydrocarbon-comprising oils of animal origin, such as perhydrosqualene;

hydrocarbon-comprising oils of plant origin, such as liquid triglycerides of fatty acids containing 4 to 10 carbon atoms, such as triglycerides of heptanoic or octanoic acids, or alternatively sunflower, maize, soybean, hazelnut, apricot, macadamia, castor or avocado oils, triglycerides of caprylic/capric acids, such as those sold by the company Stéarineries Dubois or those sold under the names Miglyol 810, 812 and 818 by the company Dynamit Nobel, jojoba oil or karite butter;

linear or branched hydrocarbons of mineral or synthetic origin, such as liquid paraffins and their derivatives, hydrogenated isoparaffins, which may or may not be volatile, petrolatum, polydecenes, purcellin oil or hydrogenated polyisobutene, such as parleam;

synthetic esters and ethers, such as oils of formula $R_1COOR_2$ in which $R_1$ represents the residue of a higher fatty acid comprising from 6 to 29 carbon atoms and $R_2$ represents a hydrocarbon-comprising chain comprising from 3 to 30 carbon atoms, such as purcellin oil, isopropyl myristate, 2-ethylhexyl palmitate, 2-octyidodecyl stearate, isostearyl isostearate, arachidyl propionate or 2-octyidodecyl benzoate; hydroxylated esters, such as isostearyl lactate, octyl hydroxystearate, octyldodecyl hydroxystearate, diisostearyl malate or triisocetyl citrate; or polyol esters, such as propylene glycol dioctanoate, neopentyl glycol diheptanoate, diethylene glycol diisononanoate and pentaerythritol esters;

fatty alcohols having from 12 to 26 carbon atoms, such as octyidodecanol, 2-butyloctanol, 2-hexyldecanol, 2-undecylpentadecanol, oleyl alcohol or cetyl alcohol;

their mixtures.

The silicone oils which can be used in the invention are in particular polymethylsiloxanes with a linear or cyclic structure which are liquid or pasty at room temperature, such as polydimethylsiloxanes, such as hexamethyidisiloxane, octamethylcyclopentasiloxane or decamethylcyclopentasiloxane, phenyl dimethicones, phenyl trimethicones and polymethylphenylsiloxanes, or their mixtures.

The solid or semi-solid fatty phase optionally present in the composition comprises in particular waxes and/or gums. The waxes and the gums which can be used in the invention are in particular microcrystalline waxes and silicone gums.

The total fatty phase can represent from 5 to 90% of the total weight of the finished product and better still from 10 to 80%.

The composition of the invention advantageously comprises colouring materials and in particular a particulate phase generally present in a proportion of 0.05 (or even 0%) to 35% of the total weight of the composition, preferably of 2 to 25%, and which can comprise pigments and/or pearlescent agents commonly used in cosmetic products. This phase can result in a coloured, white or colourless product. Mention may be made, as pigment which can be used in the composition of the invention, of titanium, zirconium or cerium oxides, as well as zinc, iron or chromium oxides, ferric blue, carbon black and barium, strontium, calcium or aluminium lakes.

The composition according to the invention can comprise, in addition, the ingredients commonly used in cosmetics, chosen as a function of the activity or of the cosmetic effect desired for the final product, such as coverage, transparency, maftness and/or satin appearance. Mention may be made, without implied limitation, of:

- lipophilic or hydrophilic thickeners, such as modified clays known under the names of bentone; aluminium fatty salts; carboxymethylcellulose; or polyacrylamides;
- vitamins, such as tocopherols and their derivatives, including the acetate, vitamin A and its derivatives, or vitamin C and its derivatives, such as the fatty esters, including the palmitate;
- sunscreening agents, such as octyl methoxycinnamate (Parsol MCX), 3-benzophenone (Uvinul M40®) or butylmethoxydibenzoylmethane (Parsol 1789®);
- lecithin, fragrances, essential oils, ceramides, preservatives or antioxidants;
- moisturizing agents, such as propylene glycol, glycerol or even ethanol;
- agents which act on greasy skin and/or antiseborrhoeic agents, such as copper and/or zinc salts.

The composition can also comprise a surfactant, for example a conventional anionic or non-ionic surfactant. The surfactant is preferably present in a proportion of 0.3 (or even 0%, in an anhydrous composition) to 8% of the total weight of the composition. Mention may be made, as surfactant which can be used in the composition of the invention, of polysorbate 40, glycerol monostearate or dimethicone copolyols with an oxypropylenated and/or oxyethylenated chain.

The processes for manufacturing the compositions according to the invention do not differ in any way from the processes conventionally used in cosmetics and are fully known to a person skilled in the art.

In the examples below, the amount of the ingredients is given as percentage by weight.

EXAMPLE 1

Anhydrous Anti-sun Care

Phase 1a:
  Tospearl 145 A 6
Phase 2a:
  Gransil SR 5 CYC (containing 25% of crosslinked siloxane) 40.0
Liquid fatty phase:
  Cyclomethicone 44.0
  Octyl methoxycinnamate 5.0
  Plant perhydrosqualene 5.0
  Fragrance q.s.

This composition is obtained by dispersing the phase 1a in the liquid phase at room temperature and with stirring and by then adding the phase 2a, still while stirring. This composition has the appearance of a translucent, non-greasy and soft gel. It is stable for 2 months at 45° C.

EXAMPLE 2

W/O Foundation

Phase 1b:
  Micropearl M 100 5
Phase 2b:
  KSG 16 (containing 24% of crosslinked siloxane) 25.0
Liquid fafty phase:
  Dimethicone copolyol 0.5
  Cyclomethicone 4.5
  Octyl methoxycinnamate 2.0
  Liquid PDMS 30.0
  Hydrogenated isoparaffin 5.0
  Fragrance q.s.
Colouring phase:
  $TiO_2$ 4.0
  Iron oxides 0.8
Aqueous phase:
  Glycerol 10.0
  Demineralized water 15.0
  Preservatives q.s.

This composition is obtained by successively dispersing the colouring phase, the phase 1b and then the phase 2b in the liquid phase at room temperature and with stirring. The aqueous phase is subsequently emulsified in the fatty phase in a turbo mixer at room temperature. This composition has the appearance of a tinted, non-greasy and soft cream. It is stable for 2 months at 45° C.

Example 3

W/O Care Cream

Phase 1c:
  Trefil E 506C (100% active material) 2
Phase 2c:
  Gransil SR 5 CYC (containing 25% of crosslinked siloxane) 8.0
Liquid fatty phase:
  Polysorbate 40 2.0
  Glycerol monostearate 2.0
  Cetyl alcohol 1.0
  Cyclomethicone 2.0
  Dimethicone 2.0
  Avocado oil 2.0
  Soybean oil 3.0
  Antioxidant (vitamin E) 0
Aqueous phase:
  Glycerol 5.0
  Polyacrylamide (hydrophilic gelling agent) 0.7
  Carboxymethylcellulose 0.5
  Demineralized water q.s. for 100
  Preservative and fragrance q.s.

The starting point is the emulsification of the aqueous phase in the fatty phase in a turbo mixer at 65° C. The phase 1c and then the phase 2c are successively added to the emulsion in a turbo mixer at 50° C. with stirring. The mixture is allowed to cool. This composition has the appearance of a white, non-greasy and soft cream. It is stable for 2 months at 45° C.

Example 4

Test of use of a Make-up Base

This composition is identical to the foundation of Example 2, without the colouring phase.
People in the test: 80 women, who are users of foundation
Duration of the test: 1 week
The make-up base is applied before the foundation and a comparison is made with and without make-up base.
The results are as follows:

|  | Without Base (complete agreement) | With Base (complete agreement) |
| --- | --- | --- |
| The skin is matt | 76% | 94% |
| The skin is soft | 49% | 88% |
| The skin is smooth | 40% | 80% |
| The make-up holds all day | 74% | 95% |

From this test, it clearly emerges that the composition of the invention confers, on the make-up, improved properties of hold over time, of comfort and of softness.

We claim:
1. A composition, comprising:
   (a) at least one liquid fatty phase associated with a solid phase comprising particles of at least one partially or completely crosslinked elastomeric organopolysiloxane, wherein said particles in the said phase represent at least 10% of the total weight of the fatty phase and;
   (b) spherical organic particles other than the particles in (a) with a particle diameter of less than 10 $\mu$m,
   wherein the ratio by weight of the organic spherical particles to.the elastomeric organopolysiloxane particles ranges from 0.25:1.1, and wherein the combined amount of said particles of elastomeric organopolysiloxane and spherical organic particles (b) is at least 20% by weight of the total weight of the fatty phase, and
   wherein the composition comprises a continuous fatty phase.
2. A composition according to claim 1, wherein the organopolysiloxane is obtained by addition and crosslinking reaction, in the presence of a platinum catalyst of:
   (a) at least one organopolysiloxane having at least two lower alkenyl groups per molecule; and
   (b) at least one organopolysiloxane having at least two hydrogen atoms bonded to a silicon atom per molecule.
3. A composition according to claim 1, wherein the organopolysiloxane is chosen from:
   i) organopolysiloxanes comprising $R_2SiO$ and $RSiO_{1.5}$ units and optionally $R_3SiO_{1.5}$ and/or $SiO_2$ units in which the R radicals, independently of one another, denote a hydrogen, an alkyl, an aryl, or an unsaturated aliphatic group, and where the ratio by weight of the $R_2SiO$ units to the $RSiO_{1.5}$ units varies from 1:1 to 30:1; and
   ii) organopolysiloxanes which are insoluble and which can be swollen in a silicone oil, obtained by addition of an organohydropolysiloxane (1) and of an organopolysiloxane (2) having unsaturated aliphatic groups, so that the amount of hydrogen or of unsaturated aliphatic groups in (1) and (2) respectively ranges from 1 to 20 mol % when the organopolysiloxane is noncyclic and from 1 to 50 mol % when the organopolysiloxane is cyclic.
4. A composition according to claim 1, wherein the spherical organic particles have a particle diameter of less than 5 $\mu$m.
5. A composition according to claim 1, wherein the spherical organic particles are chosen from microbeads of methylsilsesquioxane resins, microbeads of poly(methyl methacrylate)s, spherical particles of crosslinked polydimethylsiloxanes, spherical particles of polyamide, polystyrene microspheres and mixtures thereof.
6. A composition according to claim 1, wherein the spherical organic particles are chosen from polymeric organic particles.
7. A composition according to claim 1, wherein the ratio by weight of the spherical organic particles to the elastomeric organopolysiloxane particles ranges from 0.4:1 to 0.7:1.
8. A composition according to claim 1, wherein the liquid fatty phase comprises at least one oil chosen from silicone oils and hydrocarbon comprising oils.
9. A composition according to claim 1, wherein the liquid fatty phase comprises at least one oil chosen from hydrocarbon-comprising oils of animal, plant, mineral and synthetic origin, fatty alcohols and polymethylsiloxanes.
10. A composition according to claim 1, wherein the composition additionally comprises a solid or semi-solid fatty phase.
11. A composition according to claim 1, wherein the composition is in the form of an anhydrous gel or of a water-in-oil emulsion.
12. A composition according to claim 1, wherein said composition is a cosmetic or dermatological composition.
13. A composition according to claim 1, wherein said composition is a composition for caring for, treating, making up or removing make-up from the skin, mucous membranes or keratinous fibres.
14. A composition according to claim 1, wherein said composition additionally comprises at least one ingredient chosen from sunscreening agents, essential oils, vitamins, antiseborrhoeic agents, marine extracts, emollients, antioxidants, hydrophilic thickeners, lipophilic thickeners, preservatives, fragrances, and colouring materials.
15. A composition according to claim 1, wherein said composition is a care or make-up base for the skin or the lips.
16. A method for stabilizing a composition comprising at least one liquid fatty phase and further comprising spherical organic particles with a particle diameter of less than 10 $\mu$m, comprising the step of associating with said at least one liquid fatty phase a solid phase containing particles other than said spherical organic particles of at least one partially or completely crosslinked elastomeric organopolysiloxane, said organopolysiloxane particles representing at least 10% of the total weight of said fatty phase,
   wherein the ratio by weight of the organic spherical particles to the elastomeric organopolysiloxane particles ranges from 0.25:1.1, and wherein the combined amount of said particles of elastomeric organopolysiloxane and spherical organic particles is at least 20% by weight of the total weight of said fatty phase, and
   wherein said composition comprises a continuous fatty phase.

17. A method for rendering homogeneous a composition comprising at least one liquid fatty phase and further comprising spherical organic particles with a particle diameter of less than 10 µm, comprising the step of associating with said at least one liquid fatty phase a solid phase containing particles other than said spherical organic particles of at least one partially or completely crosslinked elastomeric organopolysiloxane, said organopolysiloxane particles representing at least 10% of the total weight of said fatty phase, wherein the ratio by weight of the organic spherical particles to the elastomeric organopolysiloxane particles ranges from 0.25:1.1, and wherein the combined amount of said particles of elastomeric organopolysiloxane and spherical organic particles is at least 20% by weight to the total weight of said fatty phase, and wherein said composition comprises a continuous fatty phase.

18. A method according to claim 16, wherein the organopolysiloxane is obtained by addition and crosslinking reaction, in the presence of a platinum catalyst of:

(a) at least one organopolysiloxane having at least two lower alkenyl groups per molecule; and (b) at least one organopolysiloxane having at least two hydrogen atoms bonded to a silicon atom per molecule.

19. A method according to claim 17, wherein the organopolysiloxane is obtained by addition and crosslinking reaction, in the presence of a platinum type catalyst of:

(a) at least one organopolysiloxane having at least two lower alkenyl groups per molecule; and (b) at least one organopolysiloxane having at least two hydrogen atoms bonded to a silicon atom per molecule.

20. A method according to claim 16, wherein the organopolysiloxane is chosen from:

i) organopolysiloxanes comprising $R_2SiO$ and $RSiO_{1.5}$ units and optionally $R_3SiO_{0.5}$ and/or $SiO_2$ units in which the R radicals, independently of one another, denote a hydrogen, an alkyl, an aryl, or an unsaturated aliphatic group, and where the ratio by weight of the $R_2SiO$ units to the $RSiO_{1.5}$ units varies from 1/1 to 30/1;

ii) organopolysiloxanes which are insoluble and which can be swollen in a silicone oil, obtained by addition of an organohydropolysiloxane (1) and of an organopolysiloxane (2) having unsaturated aliphatic groups, so that the amount of hydrogen or of unsaturated aliphatic groups in (1) and (2) respectively ranges from 1 to 20 mol % when the organopolysiloxane is non-cyclic and from 1 to 50 mol % when the organopolysiloxane is cyclic.

21. A method according to claim 30, wherein said alkyl R radical is chosen from methyl, ethyl and propyl, wherein said aryl radical is chosen from phenyl and tolyl, and wherein said unsaturated alkyl group radical is chosen from vinyl.

22. A method according to claim 17, wherein the organopolysiloxane is chosen from:

i) organopolysiloxanes comprising $R_2SiO$ and $RSiO_{1.5}$ units and optionally $R_3SiO_{0.5}$ and/or $SiO_2$ units in which the R radicals, independently of one another, denote a hydrogen, an alkyl, an aryl, or an unsaturated aliphatic group, and where the ratio by weight of the $R_2SiO$ units to the $RSiO_{1.5}$ units varies from 1/1 to 30/1;

ii) organopolysiloxanes which are insoluble and which can be swollen in a silicone oil, obtained by addition of an organohydropolysiloxane (1) and of an organopolysiloxane (2) having unsaturated aliphatic groups, so that the amount of hydrogen or of unsaturated aliphatic groups in (1) and (2) respectively ranges from 1 to 20 mol % when the organopolysiloxane is non-cyclic and from 1 to 50 mol % when the organopolysiloxane is cyclic.

23. A method according to claim 22, wherein said alkyl R radical is chosen from methyl, ethyl and propyl, wherein said aryl radical is chosen from phenyl and tolyl, and wherein said unsaturated alkyl group radical is chosen from vinyl.

24. A method according to claim 16, wherein the ratio by weight of the spherical organic particles to the elastomeric organopolysiloxane is chosen within the range from 0.4:1 to 0.7:1.

25. A method according to claim 17, wherein the ratio by weight of the spherical organic particles to the elastomeric organopolysiloxane is chosen within the range from 0.4:1 to 0.7:1.

26. A method according to claim 16, wherein the liquid fatty phase comprises at least one oil selected from silicone oils and hydrocarbon-comprising oils.

27. A method according to claim 17, wherein the liquid fatty phase comprises at least one oil selected from silicone oils and hydrocarbon-comprising oils.

28. A method according to claim 16, wherein the composition is a care or make-up base for the skin or lips.

29. A method according to claim 17, wherein the composition is a care or make-up base for the skin or lips.

30. A method according to claim 16, wherein the composition is in the form of an anhydrous gel.

31. A method according to claim 16, wherein the spherical organic particles have a particle diameter of less than 5 µm.

32. A method according to claim 16, wherein the spherical organic particles are chosen from microbeads of methylsilsesquioxane resins, microbeads of poly(methyl methacrylate)s, spherical particles of crosslinked polydimethylsiloxanes, spherical particles of polyamide, polystyrene microspberes and mixtures thereof.

33. A method according to claim 16, wherein the spherical organic particles are chosen from polymeric organic particles.

34. A method according to claim 16, wherein the liquid fatty phase comprises at least one oil chosen from hydrocarbon-comprising oils of animal, plant, mineral and synthetic origin, fatty alcohols and polymethylsiloxanes.

35. A method according to claim 16, wherein the composition additionally comprises a solid or semi-solid fatty phase.

36. A method according to claim 16, wherein the composition is in the form of a water-in-oil emulsion.

37. A method according to claim 16, wherein said liquid fatty phase is a continuous fatty phase.

38. A method according to claim 17, wherein the composition is in the form of an anhydrous gel.

39. A method according to claim 17, wherein the spherical organic particles have a particle diameter of less than 5 µm.

40. A method according to claim 17, wherein the spherical organic particles are chosen from microbeads of methylsilsesquioxane resins, microbeads of poly(methyl methacrylate)s, spherical particles of crosslinked polydimethylsiloxanes, spherical particles of polyamide, polystyrene microspheres and mixtures thereof.

41. A method according to claim 17, wherein the spherical organic particles are chosen from polymeric organic particles.

42. A method according to claim 17, wherein the liquid fatty phase comprises at least one oil chosen from hydrocarbon-comprising oils of animal, plant, mineral and synthetic origin, fatty alcohols and polymethylsiloxanes.

43. A method according to claim 17, wherein the composition additionally comprises a solid or semi-solid fatty phase.

44. A method according to claim 17, wherein the composition is in the form of a water-in-oil emulsion.

45. A method according to claim 17, wherein said liquid fatty phase is a continuous fatty phase.

* * * * *

UNITED STATES PATENT AND TRADEMARK OFFICE
CERTIFICATE OF CORRECTION

PATENT NO. : 6,258,345 B1
DATED : July 10, 2001
INVENTOR(S) : Violaine Rouquet et al.

It is certified that error appears in the above-identified patent and that said Letters Patent is hereby corrected as shown below:

Column 7,
Line 41, "particles to the elastomeric organopolysiloxane par-" should read
-- particles to the elastomeric organopolysiloxane par- --.

Column 9, claim 21,
Line 52, "A method according to claim 30, wherein" should read -- A method according to claim 20, wherein --.

Column 10,
Line 39, "spherical particles of polyamide, polystyrene microspberes" should read -- spherical particles of polyamide, polystyrene microspheres --.

Signed and Sealed this

Sixteenth Day of April, 2002

Attest:

JAMES E. ROGAN
Director of the United States Patent and Trademark Office

Attesting Officer